(12) United States Patent
Friedrich et al.

(10) Patent No.: US 8,932,215 B2
(45) Date of Patent: Jan. 13, 2015

(54) SYSTEM AND METHOD FOR RETRACTING BODY TISSUE

(75) Inventors: Adam Friedrich, Cinnaminson, NJ (US); Jason Cianfrani, East Norriton, PA (US); Matthew Beehtel, Norristown, PA (US)

(73) Assignee: Globus Medical, Inc., Audubon, PA (US)

( * ) Notice: Subject to any disclaimer, the term of this patent is extended or adjusted under 35 U.S.C. 154(b) by 213 days.

(21) Appl. No.: 13/527,250

(22) Filed: Jun. 19, 2012

(65) Prior Publication Data

US 2013/0245384 A1     Sep. 19, 2013

Related U.S. Application Data

(63) Continuation of application No. 13/418,763, filed on Mar. 13, 2012, now Pat. No. 8,231,528.

(51) Int. Cl.
*A61B 1/32* (2006.01)
(52) U.S. Cl.
USPC .......................... 600/230; 600/228; 600/231

(58) Field of Classification Search
USPC ............................ 600/184–246; 606/389–391
See application file for complete search history.

(56) References Cited

U.S. PATENT DOCUMENTS

| | | | |
|---|---|---|---|
| 6,198,961 B1 * | 3/2001 | Stern et al. | 600/422 |
| 7,232,411 B2 * | 6/2007 | Dinkler et al. | 600/233 |

* cited by examiner

*Primary Examiner* — Mary Hoffman
*Assistant Examiner* — Christina Negrellirodrigue

(57) ABSTRACT

A retractor system includes a rail having two opposed widened rail portions separated by a narrowed portion, each widened portion engageable by a separate clamp. The clamps are configured to support the rail to a fixed surface, or to support a surgical device. Each clamp may independently be positioned or slid along the rail to a desired location without interference with a clamp on an opposing widened rail portion. A device clamp is formed of spherical mating portions which enable alignment of a surgical device along six degrees of freedom, and tightenable by securing a single fastener. A retractor blade mount enables an angular and tilting disposition of a retractor blade, as well as remote manipulation of the retractor blade.

14 Claims, 5 Drawing Sheets

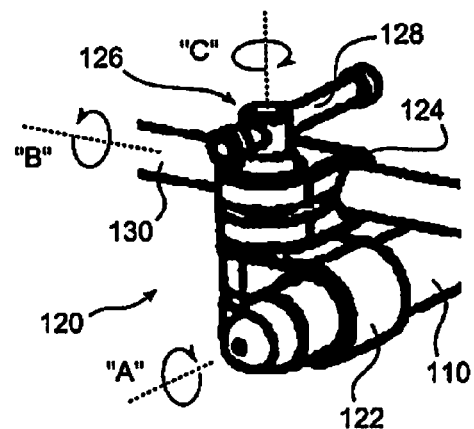
FIG. 3
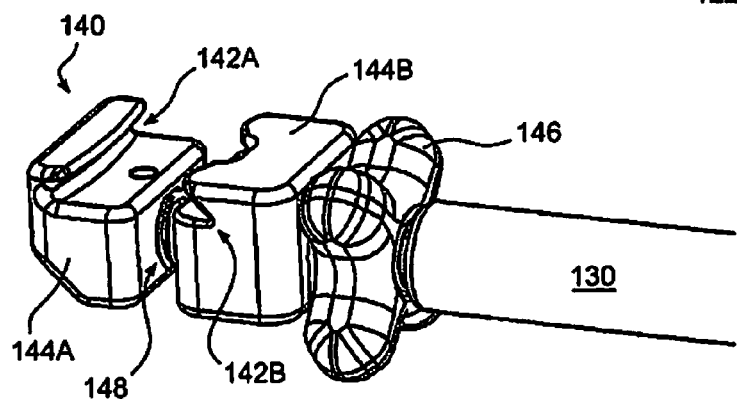
FIG. 4
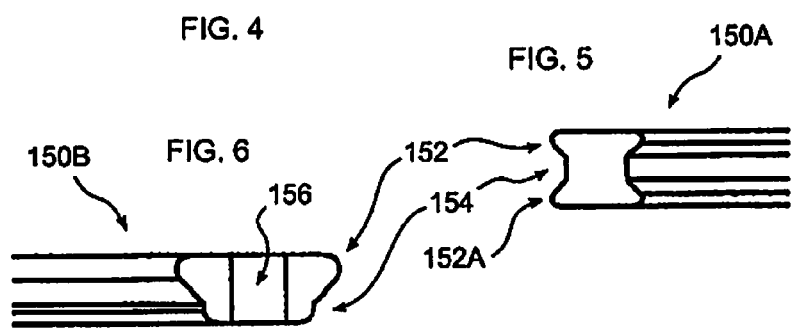
FIG. 5
FIG. 6

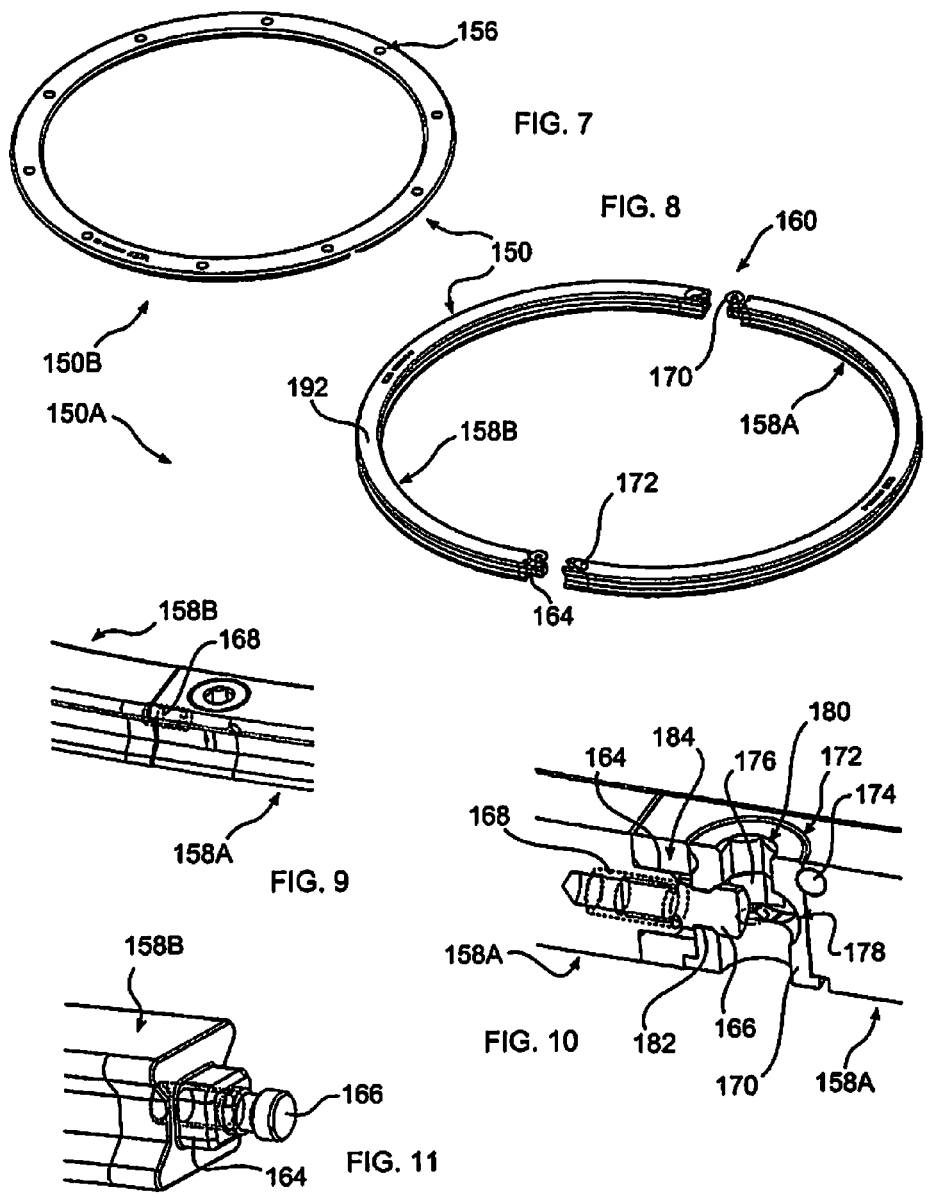

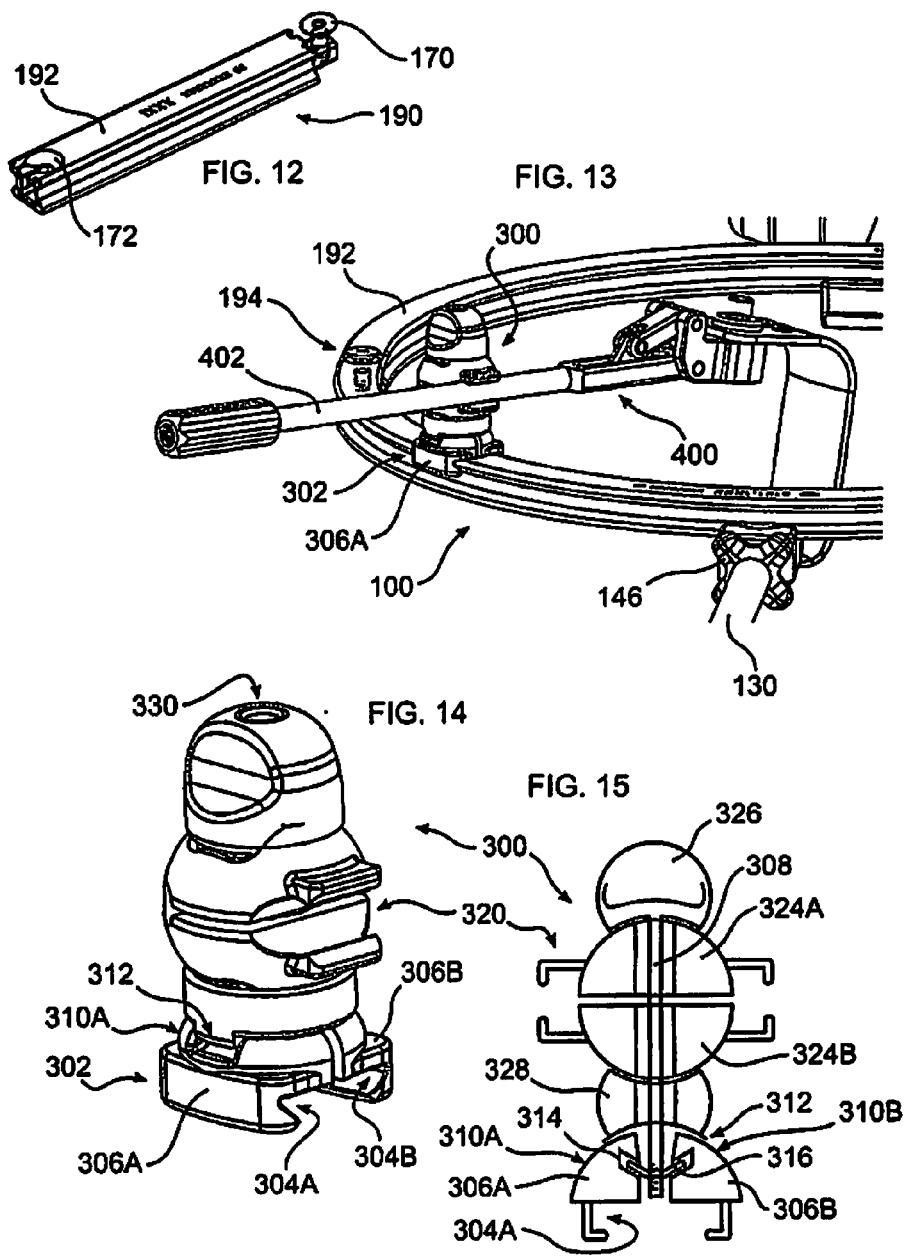

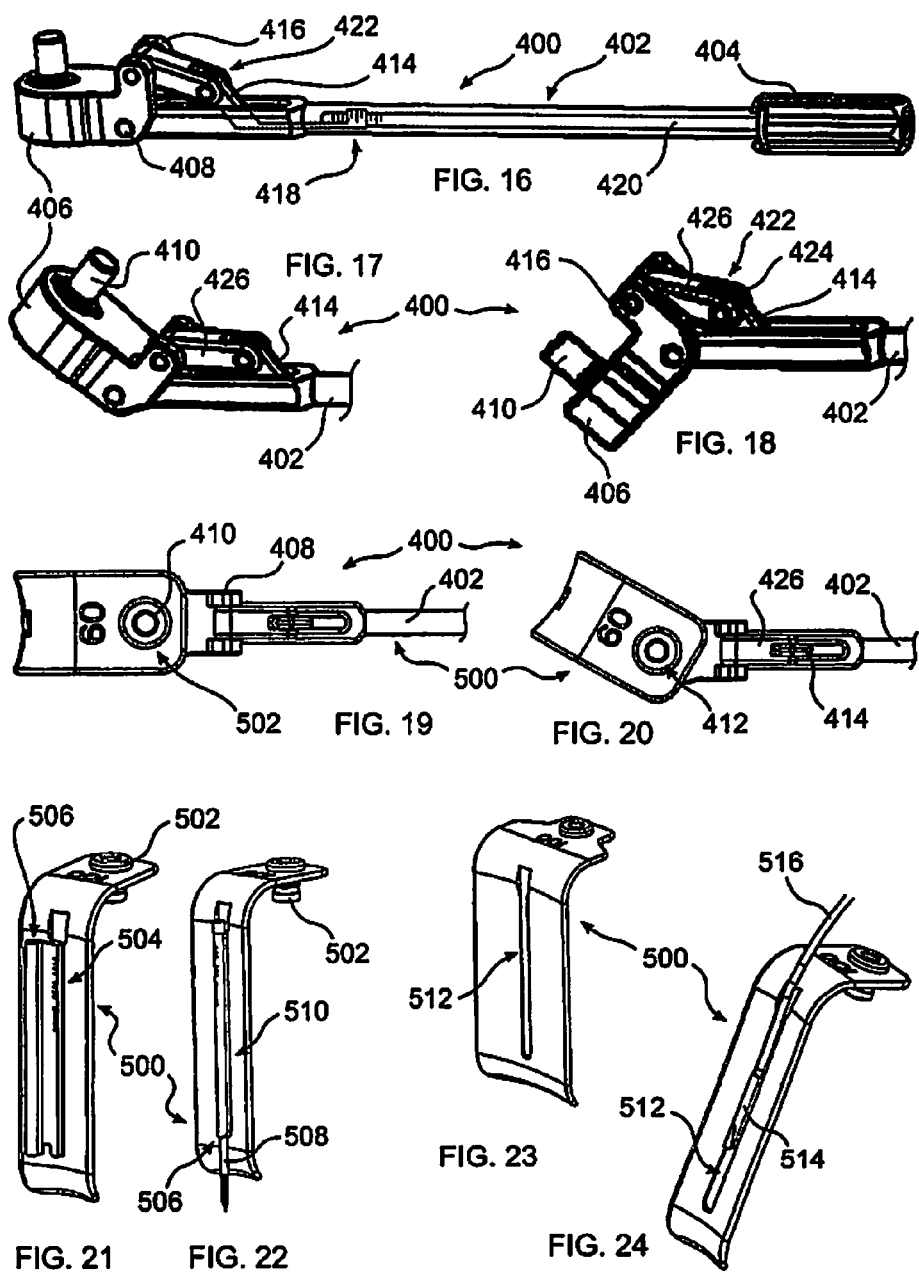

SYSTEM AND METHOD FOR RETRACTING BODY TISSUE

CROSS REFERENCE TO RELATED APPLICATIONS

This application is a continuation application of U.S. patent application Ser. No. 13/418,763 filed on Mar. 13, 2012 now U.S. Pat. No. 8,231,528, which is incorporated in its entirety herein.

FIELD OF THE INVENTION

The invention relates to a system and method for retracting body tissue during surgery, and in particular, retracting tissue during a surgical procedure involving an anterior approach to the spine.

BACKGROUND OF THE INVENTION

An anterior approach, through the abdomen, may be used to treat a variety of spine related disorders, whether inherent, or related to disease or trauma. For example, an anterior lumbar interbody fusion (ALIF) may be performed, where a portion of the annulus fibrosus and nucleus pulposus may be removed, and replaced with a stabilizing device. Alternatively, one or more spine levels may be stabilized by attachment of a flexible or rigid rod or plate to the exterior of adjacent vertebral bodies.

An anterior approach affords advantages with respect to a posterior, or posterior lateral approach, particularly in that the spinal cord is more easily avoided when accessing the vertebral body. However, there are other structures, particularly including veins and nerve branches, which must alternatively be carefully avoided. Often, two surgeons participate in an anterior approach to the spine, for example a vascular surgeon primarily responsible for the approach, and a spine surgeon responsible for the corrective spinal procedure.

A retractor moves and or retains body tissue away from a site being treated, and facilitates access to the site through or around intervening body tissue, for example the peritoneum and its contained structures. A retractor may be secured to, and supported by, the operating table, or other structure within the operating theatre.

SUMMARY OF THE INVENTION

In accordance with the disclosure, a retractor system, comprises a frame rail having a cross section defining first and second widened sections, each of the first and second widened sections having opposing surfaces, the first and second widened sections separated relative to each other by a narrowed portion; a supporting frame arm; a frame arm clamp connectable to the frame arm, and having opposed clamping surfaces each shaped to conformingly engage the opposing surfaces of the first widened section, the frame arm clamp further including a connector connecting the opposed clamping surfaces and configured to move the clamping surfaces into conforming contact with the opposing surfaces; and at least one device clamp having opposed clamping surfaces each shaped to conformingly engage the opposing surfaces of the second widened section, the device clamp further including a connector connecting the opposed clamping surfaces and configured to move the clamping surfaces into conforming contact with the opposing surfaces, the at least one device clamp slideable along the second widened section when the at least one device clamp is conformingly engaged with the second widened section and movable past the frame arm clamp when the frame arm clamp is conformingly engaged with the first widened section.

In various embodiments, the frame rail is provided in separable sections; the separable sections are joinable one to the other to form a continuous frame rail of a desired length; the separable sections each include one end forming a projection, and an opposite end forming a recess, the projection of one section positionable within a recess of another section, to thereby join separable sections into a continuous frame rail.

In other embodiments, the continuous frame rail forming an unobstructed surface along which at least one of the at least one frame arm clamp or at device clamp may slide continuously along the length of the continuous frame rail when conformingly engaged with the frame rail; the projection includes a circumferential groove, and the recess includes a rotatable bolt including a channel sized and dimensioned to receive at least a portion of the projection and mateably engage the circumferential groove within the channel; the device clamp includes a tightening fastener, and wherein the device clamp is configured to conformingly engage a surgical device and enable positioning of the device along six degrees of freedom, and after positioning the device, to secure the device and substantially prevent further movement of the surgical device upon tightening of only the tightening fastener; and the device clamp includes a plurality of mating surfaces defining spherical portions; the device clamp substantially prevents further movement of the surgical device and clamps to the frame rail upon tightening of only the tightening fastener.

In yet further embodiments in accordance with the disclosure, the retractor system further includes a retractor blade holder including: an extension having first and second opposed ends connectable to the device clamp; a mounting portion at the first end configured to support a retractor blade; and a rotatable element disposed adjacent the second end configured to enable movement of the mounting portion and attached retractor blade.

In another embodiment, a retractor system for body tissue comprises a frame rail having a cross section defining first and second widened sections, each of the first and second widened sections having opposing surfaces, the first and second widened sections separated relative to each other by a narrowed portion; a supporting frame arm connectable to a surface that is affixable relative to the body tissue; a frame arm clamp connectable to the frame arm, and having opposed clamping surfaces each shaped to conformingly engage the opposing surfaces of the first widened section, the frame arm clamp further including a connector connecting the opposed clamping surfaces and configured to move the clamping surfaces into conforming contact with the opposing surfaces by rotating a nut; and at least one device clamp having opposed clamping surfaces each shaped to conformingly engage the opposing surfaces of the second widened section, the device clamp further including a connector connecting the opposed clamping surfaces and configured to move the clamping surfaces into conforming contact with the opposing surfaces, the at least one device clamp slideable along the second widened section when the at least one device clamp is conformingly engaged with the second widened section, the at least one frame arm clamp and the at least one device clamp movable past each other along the frame rail when the at least one frame arm clamp is conformingly engaged with the first widened section and the at least one device clamp is conformingly engaged with the second widened section.

BRIEF DESCRIPTION OF THE DRAWINGS

A more complete understanding of the present invention, and the advantages and features thereof, will be more readily understood by reference to the following detailed description when considered in conjunction with the accompanying drawings wherein:

FIG. 3 depicts the table arm clamp of the system of FIG. 1;

FIG. 4 depicts the frame arm clamp of the system of FIG. 1;

FIG. 5 depicts an hour-glass cross section of the frame of FIG. 1;

FIG. 6 depicts an alternative cross section of a frame of the disclosure;

FIG. 7 depicts a frame having a cross section in accordance with FIG. 6;

FIG. 8 depicts the frame of FIG. 1, separated into sections;

FIG. 9 depicts a detailed view of assembled frame sections of the frame of FIG. 1;

FIG. 10 depicts a cross section through the center of the frame of FIG. 1, taken along the longitudinal axis of the frame;

FIG. 11 depicts a perspective view of a projecting portion of a section of a frame in accordance with FIG. 1;

FIG. 12 depicts a linear section of a frame insertable within the frame of FIG. 1;

FIG. 13 depicts a portion of the retractor system of FIG. 1, including a device clamp connected to the frame, a blade assembly connected to the device clamp, and a retractor blade connected to the blade assembly, all in accordance with the disclosure;

FIG. 14 depicts the device clamp of FIG. 13;

FIG. 15 depicts a schematic cross section of a device clamp in the manner of FIG. 14;

FIG. 16 depicts a blade assembly in accordance with FIG. 13;

FIGS. 17-18 depict alternative dispositions of a blade mount in accordance with FIG. 13;

FIG. 19 depicts a top view of the blade assembly of FIG. 13, together with a retractor blade in an aligned position;

FIG. 20 depicts the blade assembly of FIG. 19, with the retractor blade in an angled position;

FIG. 21 depicts a retractor blade of the disclosure, including an offset mount for a fastener;

FIG. 22 depicts a retractor blade of the disclosure, including a centrally aligned mount for a fastener, and an assembled fastener;

FIG. 23 depicts an alternative retractor blade of the disclosure, including a central assembly slot; and FIG. 24 illustrates a retractor blade including a light source assembled into a central slot of the disclosure.

DETAILED DESCRIPTION OF THE INVENTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

Figure 1:
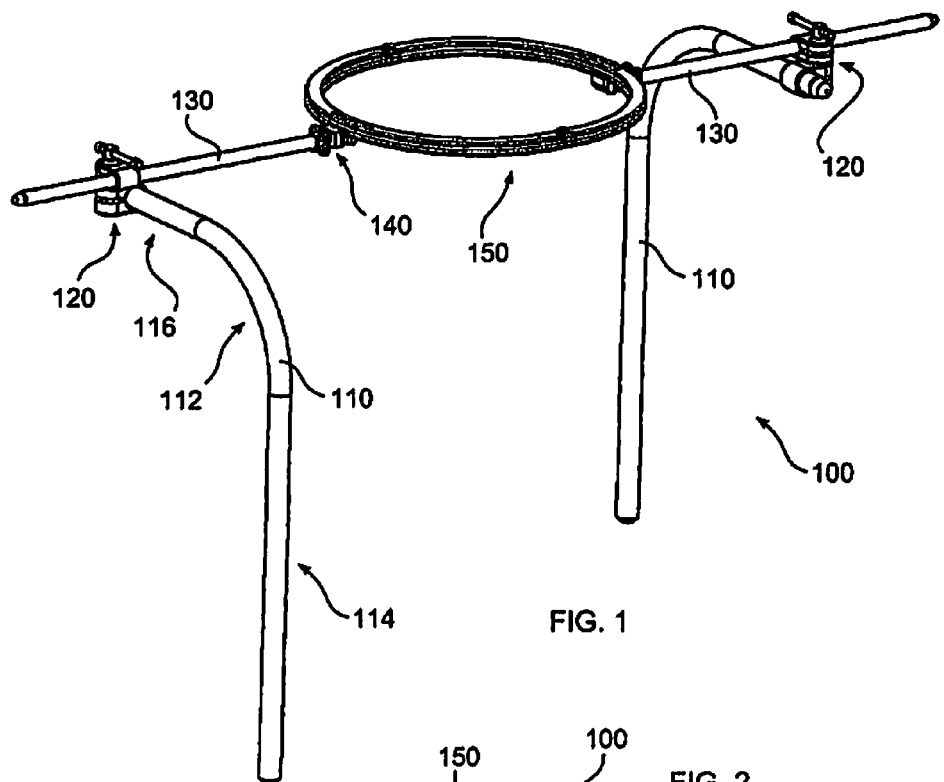
FIG. 1 depicts a retractor system in accordance with the disclosure.
Figure 2:
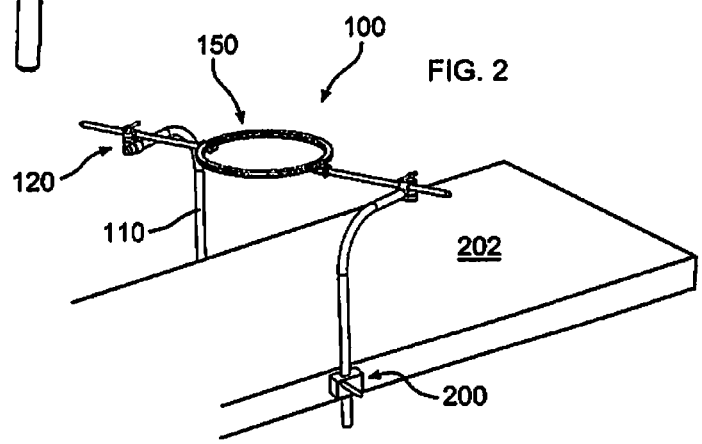
FIG. 2 depicts the retractor system of FIG. 1 connected to an operating room table.

With reference to FIGS. 1-2, in accordance with the disclosure, a retractor system 100 includes one or more each of the following: table arm 110, table arm clamp 120, a frame arm 130, a frame arm clamp 140, and frame 150. System 100 may include a table clamp 200, or may be combined with a known table clamp. For example, table arm 110 may be shaped, sized, or dimensioned to be used with any of a Clark socket, side rail socket, allen clamp, or universal clamp. Table clamp may be attached to an operating room table 202, as shown, or any other furnishing or structure in the operating theatre.

A patient, not shown, is positioned with a portion of the patient's body positioned adjacent frame 150, for example underneath frame 150. In this manner, frame 150 is advantageously located proximate a surgical site, to provide support for surgical tools or equipment, described further below. System 100 may additionally provide support for a portion of a medical practitioner's body, for example to steady a surgeon's hands.

Table arm 110 is advantageously formed as an elongated extension, slidingly received within table clamp 200, so that it may be secured within table clamp 200 at any position along table arm 110, thereby defining a distance and disposition of table arm clamp 120 with respect to table clamp 200. As table clamp 200 is positioned in a fixed position with respect to the operating theatre, a disposition of table arm clamp 120 is established with respect to the operating theatre; for example, a height of table arm clamp 120 may be adjusted and set with respect to a floor of the operating theatre.

Table arm 110 is advantageously provided with a segmented curved portion 112, whereby a table arm clamp 120 may be slidingly and rotatably positionable anywhere along a first axis defined by a first portion 114 of table arm 110, for example along a vertical axis relative to an operating table 202, or be positionable anywhere along a second axis defined by a second portion 116 of table arm 110, for example along an axis that is coplanar with operating table 202. Table arm 110 may further be rotated within table clamp 200, whereby the second portion 116 may be oriented at any angle relative to the first portion 114.

Table arm clamp 120 is detailed in FIG. 3, in which it may be seen that table arm 110 and frame arm 130 are rotatable within table arm clamp 120 about axis "A" and "B", in collars 122, 124, respectively. Frame arm 130 may further be pivoted with respect to table arm 110 about axis "C", about pivot 126. A clamp handle 128 may be used to tighten collars 122, 124, and pivot 126, for example by engaging threaded or cammed surfaces, not shown. Frame arm 130 is affixed to operating room table 200 or other object which is likewise affixable relative to body tissue of the patient, using any known or hereinafter developed means.

Frame arm 130 is advantageously formed as an elongated extension, slidingly and rotatably positionable within table arm clamp 120. A frame 150 is affixed to one or more ends of frame arm 130, or anywhere along a length of frame arm 130, using frame arm clamp 140.

With reference to FIG. 5, frame arm clamp 140 is configured to mateably engage frame 150. FIGS. 6-7 illustrate sections of two alternate forms, 150A and 150B, of frame 150.

Each of frame 150A and 150B forms relatively wide and narrow portions, 152, 154, which form an hour-glass shape, the widened sections separated from each other by a narrowed portion. Frame arm clamp 140 includes opposed clamping surfaces, or recesses 142A, 142B, which may be moved relatively apart and together, and into which opposing surfaces of wide portion 152 of frame 150 may be inserted. Alternate form 150A of frame 150 may have wide portion 152A inserted within recesses 142A, 142B, for example by inverting frame 150, or rotating frame arm clamp upon frame arm 130, to receive wide portion 152A.

To retain inserted frame 150 within frame arm clamp 140, mating clamping portions 144A, 144B are moved together to securely bind frame 150 through a mating engagement of recesses 142A, 142B with widened portion 152 or 152A. Clamping portions 144A and 144B are mutually connected by a connecting portion, depicted as frame arm 130, although a separate connector may be provided, connected to frame arm 130. To provide leverage and maintain a binding force, a lever 146 may be applied against one or both of clamping portions 144A, 144B, lever 146 moving against clamping portion 144A or 144B through movement due to engagement of threaded surfaces 148, as shown, or through interaction of cammed surfaces (not shown), or other mechanical means. In the embodiment of FIG. 5, clamping portion 144A is fixed upon frame arm 130, and clamping portion 144B slides upon frame arm 130 as lever 146 applies a moving force thereto.

In FIGS. 8-9, frames 150A and 150B are shown, wherein frame 150B is illustrated as a unitary part, having spaced apertures 156 therethrough, and frame 150A is shown without apertures 156, and divided into sections 158A and 158B. It should be understood, with reference to the following discussion, that either frame 150A or 150B may be provided with either or both of apertures, or divisible portions.

Apertures 156 are advantageously provided as an alternative or additional method for securing frame 150 to frame arm clamp 140, or to another device, whereby a fastener 194, for example a threaded fastener or clip, may be passed through aperture 156 to form a connection.

FIG. 9 illustrates a form of frame 150 which may is separable into a plurality of portions, whereby a dimension of frame 150 may be increased or decreased as needed by the medical practitioner. A connection 160 is formed between sections of frame 150. As will be understood further in the discussion of attached devices, below, it is advantageous to avoid a projection or perturbation upon the exterior surfaces of frame 150. A fastener, such as a threaded screw (not shown), or fastener 170, may be passed through section 158A, to engage a projection 164 of section 158B, to thereby fasten sections 158A and 158B together.

FIGS. 10-12 detail a manner of connecting frame 150 sections 158A and 158B, in accordance with the disclosure. A grooved post 166 extends from projection 164, and may be inserted into a post aperture 168 in frame 150, as illustrated, or may be continuously formed from material of frame 150. A bolt 170 is insertable within a bolt aperture 172 formed in section 158A. After bolt 170 is inserted into bolt aperture 172, a split ring or pin 174 is inserted into an opening in section 158A to engage a groove 176 formed upon bolt 170, to thereby rotatably retain bolt 170 within bolt aperture 172. A channel 176 having an enlarged opening 178 is formed in a side surface of bolt 172 of sufficient size and dimension to pass an end portion of post 166 into an interior of bolt 172. As bolt 170 is rotated, through interaction of tool engaging recess 180, circumferentially extending channel 176 narrows to mateably connect and engage post groove 182 and thereby secure frame sections 158A and 158B together. Projection 164 provides further stabilization and support, conformingly engaging a mating receptacle 184 in section 158A. It should also be understood that frame sections may be joined by a threaded screw 194, as illustrated in FIG. 13.

In accordance with the disclosure, sections of frame 150, for example sections 158A and 158B, extension 190, or segments having different shapes than these examples, may be joined together to form a continuous rail of any length or shape, to suit the needs of the medical practitioner. The unobstructed surface 192 of frame 150, including extensions, enables the positioning of frame arm clamps 140 and device clamps 300, or other frame rail attachments, anywhere along the length of the joined segments or extensions.

With reference to FIG. 12, a frame extension 190 is formed with connection 160 components at each end, with one end matching the connection 160 components of frame section 158A, and the other end matching the connection 160 components of frame section 158B. In this manner, two frame extensions 190 may be interposed between frame sections 158A and 158B, to increase a linear length of a supporting surface 192 of frame 150. Frame extension 190 is illustrated as a linear form in FIG. 12, although other forms, including curved forms, may be provided, to form a frame having any of a wide variety of sizes and shapes. It should further be understood that frame sections 158A and 158B may be provided with ends formed in the manner of frame extension 190, wherein one end includes projection 164, and the opposite end includes bolt aperture 172. In this manner, sections 158A and 158B may be identical, and may be used as extensions, as well.

Referring now to FIGS. 13-15, system 100 includes a device clamp 300 operative to securely hold a device with respect to frame 150 at a particular desired angular disposition. Device clamp includes a mounting base 302 comprising opposed clamping surfaces, or recesses 304A and 304B, which are sized and dimensioned to engage widened portion 152 of frame 150, and are disposed upon separable device clamping portions 306A and 306B. In one embodiment of the disclosure, device clamping portions 306A and 306B are driven together to clamp frame 150 in the manner of clamping portions 144A and 144B, securing frame arm 130, as illustrated in FIG. 5. In the embodiment illustrated in FIGS. 14 and 15, an elongated fastener 308 draws ramped clamping surfaces 310A and 310B against a complementary surface, driving device clamping portions 306A and 306B towards each other, and thereby reducing a distance between recesses 304A and 304B, to grasp frame 150. An extending surface 312 may be provided to increase leverage and a range of movement of device clamping portions 306A, 306B. An additional ramped surface 314 may be formed within an interior of device clamping portions 306A, 306B, in the embodiment shown complementary to a nut 316. it should be understood, however, that nut 316 may be positioned at an opposite end of fastener 308. FIG. 15 illustrates the device clamp of FIG. 14 schematically, in a cross-section through a central longitudinal axis of blade handle clamp 300.

In accordance with the disclosure, when device clamp 300 and frame arm clamp 140 are both assembled onto frame 150, they may each be moved independently past the other without mutual interference. More particularly, device clamp 300 may be conformingly engaged with widened portion 152, and frame arm clamp 140 conformingly engaged with widened portion 152A, and if either or both are not fully tightened to be immovable, they may be slid along frame 150 to a desired location, without interference or impediment to movement of the other, after which they may be tightened to secure against further movement. It should further be understood that device clamp 300 may alternatively be connected to widened portion 152A, and frame arm clamp 140 connected to widened portion 152, with a similar lack of mutual interference with respect to frame rail 150.

One or more blade handle clamps 320 extend from device clamp 300, operative to support a blade assembly 400, and advantageously, a blade handle 402. In FIG. 14, blade handle clamp 320 is shaped to form a shaped opening which can be closed to securely and conformingly grasp blade handle 402. In one embodiment, the shape is circular or cylindrical, so that blade handle 402 may be rotated within a loosened blade handle clamp 320, and then secured at any angular disposition when blade handle clamp 320 is tightened. As may be seen in FIG. 15, blade handle clamp 320 is formed with separable blade handle clamping portions 324A, 324B, which may be drawn together in the manner shown in FIG. 5. Alternatively, as illustrated in FIGS. 14-15, fastener 308 forms a clamp which passes through blade handle clamping portions 324A, 324B and is operative to apply a compressive force to opposed external surfaces of portions 324A, 324B, thereby drawing the portions together to grip blade handle 402.

Fastener 308 may be rigid, or is advantageously flexible, to increase a range of angular disposition of device clamp 300. A fastener handle 326, shaped to be grasped by the gloved hand of a medical practitioner, extends from an end of fastener 308. In the embodiment illustrated, fastener handle 326, blade handle clamping portions 324A and 324B, an intermediate spacer 328, and blade assembly portions 306A, 306B are provided with rounded surfaces complementary to adjacent surfaces, for example spherical portions, so that a constant or predictable amount of surface area engagement is maintained regardless of an angular disposition of these elements with respect to each other. A tool engagement aperture 330 is provided to matingly engage a driving tool, handle, or lever (not shown) for tightening fastener 308. In accordance with the foregoing, device clamp 300 enables engaging a surgical device and positioning of the device along six degrees of freedom, more particularly forward/backward, up/down, left/right (translation in three perpendicular axes) combined with rotation about three perpendicular axes (pitch, yaw, roll), and after positioning the device, to secure the device and substantially prevent further movement of the surgical device upon tightening of only one tightening fastener 308.

It should be understood that any clamped surfaces of the disclosure may be knurled, roughened, or textured, in order to promote a stable clamped connection.

With reference to FIGS. 16-24, blade assembly 400 includes blade handle 402, adjustment knob 404 rotatably mounted to a first end of handle 402, and a blade mount 406 pivotally mounted to an opposite end of blade handle 402, at pivot 408. A mounting post 410 supports one or more blades 500, and is advantageously provided with a quick release mechanism, for example a ball lock with actuating button or pin, or a spring loaded ball (not shown). Other blade attachment mechanisms may be used, as currently known and understood within the art, or as hereinafter invented.

As may be seen in FIGS. 19-20, a blade 500 is pivotally mounted to mounting post 410, so that an angular disposition of blade 500 may be achieved, with respect to handle 402. In one embodiment, blade 500 is provided with a blade mounting aperture 502. Alternatively, mounting post 410 may be an aperture, and blade mounting aperture 502 may be a post. A locking mechanism is provided to secure blade 500 at a particular angular orientation. For example, a tool engaging threaded connector 412 may be associated with mounting post 410, or blade 500. Alternatively, mounting post 410 may be provided with a splined surface, mateably engageable with blade mounting aperture 502, so that blade 500 may advantageously be inserted at a desired angular disposition, which angle is maintained by the splined engagement.

In FIG. 16, a movable coupling 414 is pivotally connected to an offset pivot 416, which is connected to pivot 408. As movable coupling 414 is moved forward or rearward axially with respect to handle 402, offset pivot 416 is caused to rotate radially with respect to pivot 408, thereby changing a tilting angle of blade mount 406 with respect to handle 402. In the embodiment shown, the tilting angle is at 90 degrees with respect to the angular disposition obtainable by the connection of mounting post 410 and blade mounting aperture 502. In the embodiment of FIG. 16, movable coupling 414 is caused to move through a threaded connection 418, formed between an end of movable coupling 414 and a threaded portion 420 connected to adjustment knob 404. Adjustment knob 404 is rotatably mounted to handle 402, whereby rotation of adjustment knob 404 in a first direction rotates threads of threaded connection 418 to draw movable coupling in a direction towards adjustment knob 404, thereby pulling upon offset pivot 416, which functions as a lever pivoting upon pivot 408 to tilt blade mount 406. Turning adjustment knob in a second direction causes an opposite movement of offset pivot 416 and blade mount 406. In use, it may be advantageous to position all components of retraction system 100, with blade 500 contacting body tissue to be retracted, after which adjustment knob 404 is rotated to cause blade mount 406 to pivot, and to thereby cause attached blade 500 to move body tissue away from an access site.

Although threaded connection 418 is illustrated nearer to blade mount 406 than adjustment knob 404, threaded connection 418 could be located anywhere along handle 402, including within an interior of adjustment knob 404. Additionally, instead of threads, threaded connection 418 may use ramps, cams, or other methods of causing movement of movable coupling 414, and may further include an electric or hydraulic actuator.

Linkage 422 may advantageously be provided, connected between offset pivot 416 and movable coupling 414, to increase a range of motion of blade mount 406, and or to decrease a size of blade assembly 400. In the embodiment shown, linkage 422 includes a linkage pivot 424, and a link extension 426 pivotally mounted to offset pivot 416 and linkage pivot 424.

Referring now to FIGS. 21-24, a blade 500 is sized and dimensioned to move and or retain body tissue in a desired location. Blade 500 may have any size and shape that is known or hereinafter is found to have a therapeutic purpose, including as examples long, short, wide, narrow, trapezoidal, concave, convex, odontoid, and Harrington, Deaver, Yu-Holtgrewe, and Carol. Typical sizes include, as examples, widths between 16 and 50 mm widths, and lengths between 40 and 220 mm, although blade 500 may be substantially narrower, wider, shorter, or longer, dictated only by the needs of the medical (including veterinary) practitioner. A shaped tip may be provided to more securely engage bodily tissue or structures, and blade 500 may be malleable, so that an optimal conformity with body tissue or surgical equipment may be achieved. Blade 500 may be formed of any biocompatible material, including a polymer or metallic material, including, as examples, high molecular weight polyethylene or titanium, stainless steel, or aluminum.

In the embodiment shown in FIG. 21, a fastener bracket 504 is positioned offset from a longitudinal centerline of blade 500. In FIG. 22, bracket 510 is positioned centered with respect to a longitudinal centerline of blade 500. A channel 506 formed within bracket 504 or 510 supports a fastener 508, as illustrated in FIG. 22. In one embodiment, bracket 504 is hinged, so that channel 506 may be moved with respect to a longitudinal centerline of blade 500. Alternatively bracket 504 may be fixed to a left or right of a centerline of blade 500. Accordingly, a medical practitioner may choose a blade having a channel 506 positioning, or may reposition channel 506, to align a supported fastener 508 with an appropriate structure within the body, suitable for receiving fastener 508, including as an example, a vertebral body.

FIG. 23 illustrates an alternative blade 500 shape, and further illustrates an elongated slot 512 through which body tissue may be viewed, and to which additional devices may be attached. FIGS. 21-22 illustrate attachment of brackets 504 or 510, and in FIG. 24, a light emitter 514 has been attached. Light emitter 514 may be provided with an internal power source, or may be connected to an electrical source with a cable 516. In other embodiments, a camera, suction device, or other tool is positioned and connected in the manner of light emitter 514. Light emitter 514 or other device may further be provided with a mounting bracket (not shown) which enables positioning of an attached device in connection with blade 500, irrespective of a position of blade 500.

The assembled components of retractor system 100 are thus adapted to provide movement of blade 500 in all degrees of freedom, in order to provide an advantageously optimal approach and trajectory into the body for surgical instrumentation, improving exposure for instrumentation and manipulation, and for location and placement of body tissue with high precision, while minimizing trauma.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A retractor system, comprising:
   a frame rail having a cross section defining first and second widened sections, each of said first and second widened sections having opposing surfaces, said first and second widened sections separated relative to each other by a narrowed portion;
   a supporting frame arm;
   a frame arm clamp connectable to said frame arm, and having opposed clamping surfaces each shaped to conformingly engage said opposing surfaces of said first widened section, said frame arm clamp further including a connector connecting said opposed clamping surfaces and configured to move said clamping surfaces into conforming contact with said opposing surfaces
   wherein said frame rail is provided in separable sections, wherein said separable sections each include one end forming a projection, and an opposite end forming a recess, the projection of one section positionable within a recess of another section, to thereby join separable sections into a continuous frame rail, wherein said projection includes a circumferential groove, and said recess includes a rotatable bolt including a channel sized and dimensioned to receive at least a portion of said projection and mateably engage said circumferential groove within said channel.

2. The retractor system of claim 1, wherein said separable sections are joinable one to the other to form a continuous frame rail of a desired length.

3. The retractor system of claim 1, the continuous frame rail forming an unobstructed surface along which at least one of said at least one frame arm clamp or at least one of at least one device clamp may slide continuously along the length of the continuous frame rail when conformingly engaged with said frame rail.

4. The retractor system of claim 3, wherein said device clamp includes a tightening fastener, and wherein said device clamp is configured to conformingly engage a surgical device and enable positioning of the device along six degrees of freedom, and after positioning the device, to secure the device and substantially prevent further movement of the surgical device upon tightening of only said tightening fastener.

5. The retractor system of claim 4, wherein said device clamp includes a plurality of mating surfaces defining spherical portions.

6. The retractor system of claim 4, wherein said device clamp substantially prevents further movement of the surgical device and clamps to said frame rail upon tightening of only said tightening fastener.

7. The retractor system of claim 1, further including a retractor blade holder including:
   an extension having first and second opposed ends connectable to a device clamp;
   a mounting portion at said first end configured to support a retractor blade; and
   a rotatable element disposed adjacent said second end configured to enable movement of the mounting portion and attached retractor blade.

8. A retractor system for body tissue, comprising:
   a frame rail having a cross section defining first and second widened sections, each of said first and second widened sections having opposing surfaces, said first and second widened sections separated relative to each other by a narrowed portion; and
   a supporting frame arm connectable to a surface that is affixable relative to the body tissue;
   a frame arm clamp connectable to said frame arm, and having opposed clamping surfaces each shaped to conformingly engage said opposing surfaces of said first widened section, said frame arm clamp further including a connector connecting said opposed clamping surfaces and configured to move said clamping surfaces into conforming contact with said opposing surfaces by rotating a nut,
   wherein said separable sections are joinable one to the other to form a continuous frame rail of a desired length, wherein said separable sections each include one end forming a projection, and an opposite end forming a recess, the projection of one section positionable within a recess of another section, to thereby join separable sections into a continuous frame rail, wherein said projection includes a circumferential groove, and said recess includes a rotatable bolt including a channel sized and dimensioned to receive at least a portion of said projection and mateably engage said circumferential groove within said channel.

9. The retractor system of claim 8, wherein said frame rail is provided in separable sections.

10. The retractor system of claim 8, said continuous frame rail forming an unobstructed surface along which at least one frame arm clamp or least one device clamp may slide continuously along the length of the continuous frame rail when conformingly engaged with said frame rail.

11. The retractor system of claim 10, wherein said device clamp includes a tightening fastener, and wherein said device clamp is configured to conformingly engage a surgical device and enable positioning of the device along six degrees of freedom, and after positioning the device, to secure the device and substantially prevent further movement of the surgical device upon tightening of only said tightening fastener.

12. The retractor system of claim 11, wherein said device clamp includes a plurality of mating surfaces defining spherical portions.

13. The retractor system of claim 11, wherein said device clamp substantially prevents further movement of the surgical device and clamps to said frame rail upon tightening of only said tightening fastener.

14. A retractor system for body tissue, comprising:
a frame rail having a cross section defining first and second widened sections, each of said first and second widened sections having opposing surfaces, said first and second widened sections separated relative to each other by a narrowed portion, said frame rail formed in separable portions, each portion including a projecting portion and a recessed portion, the projection portion mateable with the recessed portion to connect the separable portions;
a supporting frame arm connectable to a surface that is affixable relative to the body tissue;
a frame arm clamp connectable to said frame arm, and having opposed clamping surfaces each shaped to conformingly engage said opposing surfaces of said first widened section, said frame arm clamp further including a connector connecting said opposed clamping surfaces and configured to move said clamping surfaces into conforming contact with said opposing surfaces by rotating a nut;
a table arm having a first portion, a second portion and a curved portion that extends between the first portion and the second portion, wherein the first portion is elongated relative to the second portion, and
a table arm clamp for holding both the supporting frame arm and the table arm such that along a longitudinal axis of the first portion of the table arm, the second portion is in a different plane from the supporting frame arm.

* * * * *